(12) United States Patent
Hettrick et al.

(10) Patent No.: US 9,415,231 B2
(45) Date of Patent: Aug. 16, 2016

(54) CARDIAC THERAPY BASED UPON IMPEDANCE SIGNALS

(71) Applicant: Medtronic, Inc., Minneapolis, MN (US)

(72) Inventors: Douglas A. Hettrick, Andover, MN (US); Todd M. Zielinski, Ham Lake, MN (US); Eduardo Warman, Maple Grove, MN (US); Shantanu Sarkar, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/165,211

(22) Filed: Jan. 27, 2014

(65) Prior Publication Data

US 2014/0142646 A1    May 22, 2014

Related U.S. Application Data

(62) Division of application No. 12/916,012, filed on Oct. 29, 2010, now Pat. No. 8,639,328.

(51) Int. Cl.

| | | |
|---|---|---|
| *A61N 1/39* | (2006.01) | |
| *A61B 5/053* | (2006.01) | |
| *A61N 1/362* | (2006.01) | |
| *A61N 1/365* | (2006.01) | |
| *A61N 1/368* | (2006.01) | |
| *A61B 5/00* | (2006.01) | |
| *A61B 5/0452* | (2006.01) | |

(52) U.S. Cl.
CPC ............ *A61N 1/3987* (2013.01); *A61B 5/0535* (2013.01); *A61B 5/7239* (2013.01); *A61N 1/3627* (2013.01); *A61N 1/3682* (2013.01); *A61N 1/3684* (2013.01); *A61N 1/36521* (2013.01); *A61B 5/0452* (2013.01)

(58) Field of Classification Search
CPC ............ A61N 1/36521; A61N 1/3627; A61N 1/3684; A61N 1/3682; A61N 1/3987; A61B 5/7239; A61B 5/0535; A61B 5/0452
See application file for complete search history.

(56) References Cited

U.S. PATENT DOCUMENTS

| | | | |
|---|---|---|---|
| 4,428,378 A | 1/1984 | Anderson et al. | |
| 4,450,527 A | 5/1984 | Sramek | |
| 5,052,388 A | 10/1991 | Sivula et al. | |
| 5,454,377 A | 10/1995 | Dzwonczyk et al. | |
| 5,501,702 A | 3/1996 | Plicchi et al. | |
| 5,584,868 A | 12/1996 | Salo et al. | |
| 5,999,854 A | 12/1999 | Deno et al. | |
| 6,223,082 B1 | 4/2001 | Bakels et al. | |

(Continued)

FOREIGN PATENT DOCUMENTS

| | | |
|---|---|---|
| CN | 1662278 A | 8/2005 |
| EP | 0 532 149 B1 | 6/1997 |

(Continued)

OTHER PUBLICATIONS

Hall et al., *Guyton and Hall Textbook of Medical Physiology*, 12th Edition, Saunders, Philadelphia, PA, 2011; pp. 265-268.

(Continued)

*Primary Examiner* — Catherine Voorhees
(74) *Attorney, Agent, or Firm* — Carol F. Barry

(57) ABSTRACT

Methods and/or devices are disclosed herein for monitoring cardiac impedance signal and delivering therapy to a patient's heart based upon the monitored cardiac impedance.

14 Claims, 11 Drawing Sheets

(56) References Cited

U.S. PATENT DOCUMENTS

| | | |
|---|---|---|
| 7,065,400 B2 | 6/2006 | Schechter |
| 7,092,755 B2 | 8/2006 | Florio |
| 7,139,609 B1 | 11/2006 | Min et al. |
| 7,228,174 B2 | 6/2007 | Burnes et al. |
| 7,366,567 B2 | 4/2008 | Zhu et al. |
| 7,440,803 B2 | 10/2008 | Ni et al. |
| 7,548,784 B2 | 6/2009 | Chinchoy |
| 7,580,746 B2 | 8/2009 | Gilkerson et al. |
| 7,614,308 B2 | 11/2009 | Berner et al. |
| 7,650,181 B2 | 1/2010 | Freeman et al. |
| 7,657,313 B2 | 2/2010 | Rom |
| 7,684,863 B2 | 3/2010 | Parikh et al. |
| 7,689,283 B1 | 3/2010 | Schecter |
| 7,844,331 B2 | 11/2010 | Li et al. |
| 7,848,810 B1 | 12/2010 | Nabutovsky et al. |
| 7,869,871 B2 | 1/2011 | Salo et al. |
| 7,914,452 B2 | 3/2011 | Hartley et al. |
| 8,355,548 B2 | 1/2013 | Kovacs, Jr. et al. |
| 8,639,328 B2 | 1/2014 | Hettrick et al. |
| 9,199,086 B2 | 12/2015 | Zielinski et al. |
| 2001/0047194 A1 | 11/2001 | Thompson et al. |
| 2003/0204212 A1 | 10/2003 | Burnes et al. |
| 2004/0087870 A1 | 5/2004 | Jarverud |
| 2005/0165454 A1 | 7/2005 | Chinchoy |
| 2005/0203429 A1 | 9/2005 | Judy |
| 2006/0271121 A1 | 11/2006 | Ding et al. |
| 2007/0055170 A1 | 3/2007 | Lippert et al. |
| 2007/0142733 A1 | 6/2007 | Hatlestad et al. |
| 2007/0191901 A1 | 8/2007 | Schecter |
| 2007/0213778 A1 | 9/2007 | Burnes et al. |
| 2008/0103530 A1 | 5/2008 | Vitense et al. |
| 2008/0208274 A1 | 8/2008 | Zhu et al. |
| 2008/0234594 A1 | 9/2008 | Brooks et al. |
| 2008/0249375 A1 | 10/2008 | Obel |
| 2008/0249583 A1 | 10/2008 | Salo et al. |
| 2009/0043213 A1 | 2/2009 | Kovacs et al. |
| 2009/0082823 A1 | 3/2009 | Shuros et al. |
| 2009/0118783 A1 | 5/2009 | Patangay et al. |
| 2009/0270933 A1 | 10/2009 | Hettrick et al. |
| 2009/0270934 A1 | 10/2009 | Hettrick et al. |
| 2009/0275854 A1 | 11/2009 | Zielinski et al. |
| 2009/0275855 A1 | 11/2009 | Zielinski et al. |
| 2009/0292334 A1 | 11/2009 | Rom |
| 2009/0299203 A1 * | 12/2009 | De Voir et al. ............... 600/509 |
| 2010/0023078 A1 | 1/2010 | Dong et al. |
| 2010/0030086 A1 | 2/2010 | Zielinski et al. |
| 2010/0030087 A1 | 2/2010 | Hettrick et al. |
| 2010/0030292 A1 | 2/2010 | Sarkar et al. |
| 2010/0113962 A1 | 5/2010 | Hettrick et al. |
| 2010/0121403 A1 | 5/2010 | Schecter et al. |
| 2010/0179608 A1 | 7/2010 | Limousin |
| 2010/0185250 A1 | 7/2010 | Rom |
| 2011/0087301 A1 | 4/2011 | Li et al. |
| 2012/0109245 A1 | 5/2012 | Hettrick et al. |
| 2012/0239104 A1 | 9/2012 | Rosenberg et al. |
| 2013/0079839 A1 | 3/2013 | Lian et al. |
| 2015/0202443 A1 | 7/2015 | Zielinski et al. |

FOREIGN PATENT DOCUMENTS

| | | |
|---|---|---|
| EP | 1 453 572 B1 | 4/2008 |
| EP | 1 997 427 A1 | 12/2008 |
| WO | WO 2006/061822 A2 | 6/2006 |
| WO | WO 2006/061822 A3 | 4/2009 |

OTHER PUBLICATIONS

International Search Report and Written Opinion for International Application No. PCT/US2011/034486, mailed Nov. 9, 2011; 10 pgs.
U.S. Appl. No. 14/158,516, filed Jan. 17, 2014, Zielinski et al.
U.S. Appl. No. 14/158,533, filed Jan. 17, 2014, Zielinski et al.
International Search Report and Written Opinion for International Application No. PCT/US2015/011561.

* cited by examiner

CARDIAC THERAPY BASED UPON IMPEDANCE SIGNALS

This application is a divisional of patent application Ser. No. 12/916,012 filed on Oct. 29, 2010, (pending), which is incorporated herein by reference.

The disclosure herein relates to methods for monitoring impedance signals proximate a patient's heart and/or delivering therapy to the patient's heart based upon the monitored impedance signals, and further to devices for performing such processes.

Cardiac resynchronization therapy (CRT) has been clinically demonstrated to improve cardiac function in patients suffering from various cardiac conditions such as congestive heart failure. CRT may apply electrical stimulation, or pacing, to one or both ventricles and/or atria to improve cardiac chamber coordination, which in turn, may improve stroke volume, pumping efficiency, etc. The time intervals between pacing the atria and the ventricles may be referred to as the AV delay and the time interval between pacing each of the ventricles may be referred to as the VV delay.

It may be challenging for clinicians to select the optimal AV delay and VV delay to resynchronize the heart chamber contractions using CRT. A clinician may use echocardiography (e.g., ultrasound) to determine the optimal AV and VV delays that result in the best hemodynamic response. For example, ultrasound may be used to observe E-waves and A-waves, which may be representative of blood flow velocity across the mitral valve during the discrete early and late filling periods of diastole, respectively. The AV delay may be clinically adjusted to optimize the E-waves and A-waves, so that the atria are allowed to contract and fill the ventricles before the ventricles contract.

CRT systems having automated selection of AV and VV delays without clinician intervention exist. For example, systems that automatically adjust AV and VV delays may be generally disclosed in U.S. Pat. No. 6,223,082 issued to Bakels, et al., U.S. Pat. No. 7,548,784 issued to Chinchoy, and U.S. Pat. No. 7,228,174 to Burnes, et al., each of which are incorporated herein by reference in their entirety.

Impedance sensors have been used in pacing systems for obtaining information associated with cardiac function. For example, U.S. Pat. No. 5,501,702 issued to Plicchi, et al. and U.S. App. Pub. No 2009/0275854 A1 to Zielinski et al., each of which are incorporated herein by reference in their entirety, discloses measuring impedance from various electrode combinations.

SUMMARY

The disclosure herein relates to methods for monitoring various impedance signals between two or more electrodes proximate a patient's heart and delivering therapy to the patient's heart based on the various impedance signals. More specifically, one or more fiducial points may be determined based upon the real time waveform morphology of the impedance signals that relate temporarily to various mechanical cardiac events and cardiac therapy may be adjusted based upon the one or more fiducial points and/or characteristics associated with the one or more fiducial points.

One exemplary implantable medical device disclosed herein for use in delivering therapy to a patient's heart may include a sensing module configured to monitor an impedance between at least two electrodes proximate the patient's heart to provide an impedance signal, a therapy delivery module configured to deliver cardiac therapy to the patient's heart, and a control module coupled to the sensing module and the therapy delivery module. The control module may be configured to determine an E-wave portion representative of an E-wave during a cardiac cycle based on the impedance signal and determine an A-wave portion representative of an A-wave during the cardiac cycle based on the impedance signal. The control module may be further configured to deliver cardiac therapy to the patient based upon one or more characteristics associated with at least one of the E-wave portion and the A-wave portion.

In one or more embodiments of the exemplary devices disclosed herein, the control module may be further configured to determine the E-wave portion representative of the E-wave during the cardiac cycle using a derivative of the impedance signal and determine the A-wave portion corresponding to the A-wave during the cardiac cycle using the derivative of the impedance signal.

Further, in one or more embodiments of the exemplary devices disclosed herein, the control module may be further configured to determine an E-A time interval from the E-wave portion to the A-wave portion and adjust the cardiac therapy delivered to the patient based upon the E-A time interval to optimize at least one of AV delay and VV delay (e.g., adjust the cardiac therapy delivered to the patient by delaying atrial electrical stimulation by a first selected time period after a first selected fiducial point within the E-wave portion and/or adjust the cardiac therapy delivered to the patient by delaying ventricular electrical stimulation by a second selected time period after a second selected fiducial point within the A-wave portion).

Still further, in one or more embodiments of the exemplary devices disclosed herein, the control module may be further configured determine a first derivative of the impedance signal to provide a derivative signal, determine the E-wave portion using the derivative signal corresponding to the E-wave during the cardiac cycle, and determine the A-wave portion using the derivative signal corresponding to the A-wave during the cardiac cycle. In at least one embodiment, the control module may be further configured to determine at least one of an E-wave maximum value of the E-wave portion and an A-wave maximum value of the A-wave portion and adjust the cardiac therapy delivered to the patient based upon at least one of the E-wave maximum value and the A-wave maximum value to optimize at least one of AV delay and VV delay. In at least one embodiment, the control module may be further configured to determine an E-A area under at least one of the E-wave portion and the A-wave portion and adjust the cardiac therapy delivered to the patient based upon the E-A area to optimize at least one of AV delay and VV delay. In at least one embodiment, the control module is further configured to determine an E-A minimum trough value between a maximum value within the E-wave portion and a maximum value within the A-wave portion and adjust the cardiac therapy delivered to the patient based upon the E-A minimum trough value to optimize at least one of AV delay and VV delay.

Another exemplary implantable medical device disclosed herein for use in delivering therapy to a patient's heart includes, among other things, a control module that may be configured to determine one or more fiducial points based on the impedance signal or a derivative thereof. Each of the one or more fiducial points may be a fiducial point associated with a mechanical cardiac event during a cardiac cycle. The control module may be further configured to deliver cardiac therapy to the patient based upon one or more characteristics associated with the one or more fiducial points (e.g., determine a myocardial performance index based on the one or more fiducial points and adjust the cardiac therapy delivered to the patient based upon the myocardial performance index).

In one or more embodiments of the exemplary devices disclosed herein, the control module may be further configured to determine an E-wave portion based on the one or more fiducial points and determine an A-wave portion based on the one or more fiducial points.

Further, in one or more embodiments of the exemplary devices disclosed herein, the control module may be further configured to determine a time interval from a first fiducial point of the one or more fiducial points to a second fiducial point of the one or more fiducial points and adjust the cardiac therapy delivered to the patient based upon the time interval.

Still further, in one or more embodiments of the exemplary devices and methods disclosed herein, the one or more fiducial points may include a first maximum value of a derivative of the impedance signal and a second maximum value of the derivative of the impedance signal. The second maximum value may be less than the first maximum value and greater than a remainder of values of the derivative of the impedance signal.

One exemplary method disclosed herein for use in monitoring a patient may include monitoring an impedance between at least two electrodes proximate the patient's heart to provide an impedance signal, determining an E-wave portion representative of an E-wave during a cardiac cycle based on the impedance signal, determining an A-wave portion representative of an A-wave during the cardiac cycle based on the impedance signal, monitoring the E-wave portion and the A-wave portion to determine one or more characteristics of the patient, and delivering cardiac therapy to the patient based upon the one or more characteristics associated with at least one of the E-wave portion and the A-wave portion. The exemplary method may further include adjusting the cardiac therapy delivered to the patient by delaying atrial electrical stimulation by a first selected time period after a first selected fiducial point within the E-wave portion and adjusting the cardiac therapy delivered to the patient by delaying ventricular electrical stimulation by a second selected time period after a second selected fiducial point within the A-wave portion.

In one or more embodiments of the exemplary methods disclosed herein, the exemplary methods may include determining the E-wave portion representative of the E-wave during the cardiac cycle using a derivative of the impedance signal and determining the A-wave portion corresponding to the A-wave during the cardiac cycle using the derivative of the impedance signal.

Further, in one or more embodiments of the exemplary methods disclosed herein, the exemplary methods may include determining an E-A time interval from the E-wave portion to the A-wave portion and adjusting the cardiac therapy delivered to the patient based upon the E-A time interval to optimize at least one of AV delay and VV delay.

Another exemplary method disclosed herein for use in delivering therapy to a patient's heart may include monitoring an impedance between at least two electrodes proximate the patient's heart to provide an impedance signal, determining one or more fiducial points based on the impedance signal or a derivative thereof (e.g., each of the one or more fiducial points being a fiducial point associated with a mechanical cardiac event during a cardiac cycle), and delivering cardiac therapy to the patient based upon one or more characteristics associated with the one or more fiducial points.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
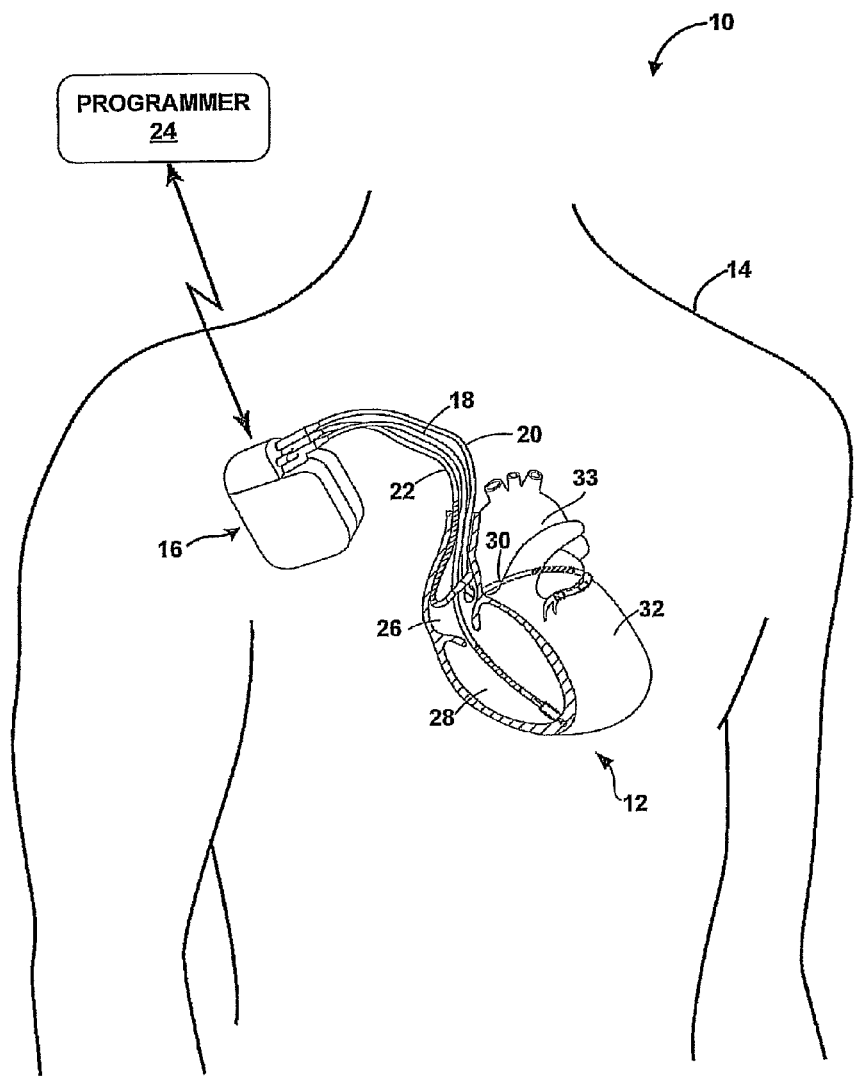
FIG. 1 is a diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-11. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual diagram illustrating an exemplary therapy system 10 that may be used to monitor a patient's heart 12 and/or deliver cardiac therapy to the patient 14. Patient 14 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that may provide electrical stimulation to the patient's heart 12 via electrodes coupled to one or more of the leads 18, 20, 22.

The leads 18, 20, 22 extend into the heart 12 of the patient 14 to sense electrical activity of the heart 12 and/or deliver electrical stimulation to the heart 12. In the example shown in FIG. 1, the right ventricular (RV) lead 18 extends through one or more veins (not shown), the superior vena cava (not shown), the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins, the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing pulses to the heart 12 based on the electrical signals sensed within the heart 12. The configurations of the electrodes used by the IMD 16 for sensing and pacing may be unipolar or bipolar. The IMD 16 may also provide cardiac resynchronization therapy, defibrillation therapy, and/or cardioversion therapy via electrodes located on at least one of the leads 18, 20, 22. Further, the IMD 16 may detect arrhythmia of the heart 12, such as fibrillation of the ventricles 28, 32 and may deliver defibrillation therapy to the heart 12 in the form of electrical pulses. In some examples, the IMD 16 may be programmed to deliver a progression of therapies, e.g., pulses with increasing energy levels, until a fibrillation of the heart 12 is stopped. Further, the IMD 16 may detect tachycardia and/or fibrillation employing one or more tachycardia and/or fibrillation detection techniques known in the art.

In some examples, the programmer 24 may be a handheld computing device or a computer workstation, which a user, such as a clinician (e.g., a physician, a technician, etc.) and/or patient may use to communicate with the IMD 16. For example, the user may interact with the programmer 24 to retrieve physiological and/or diagnostic information (e.g., impedance signals, E-A waveforms determined based on impedance signals, etc.) from the IMD 16.

The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
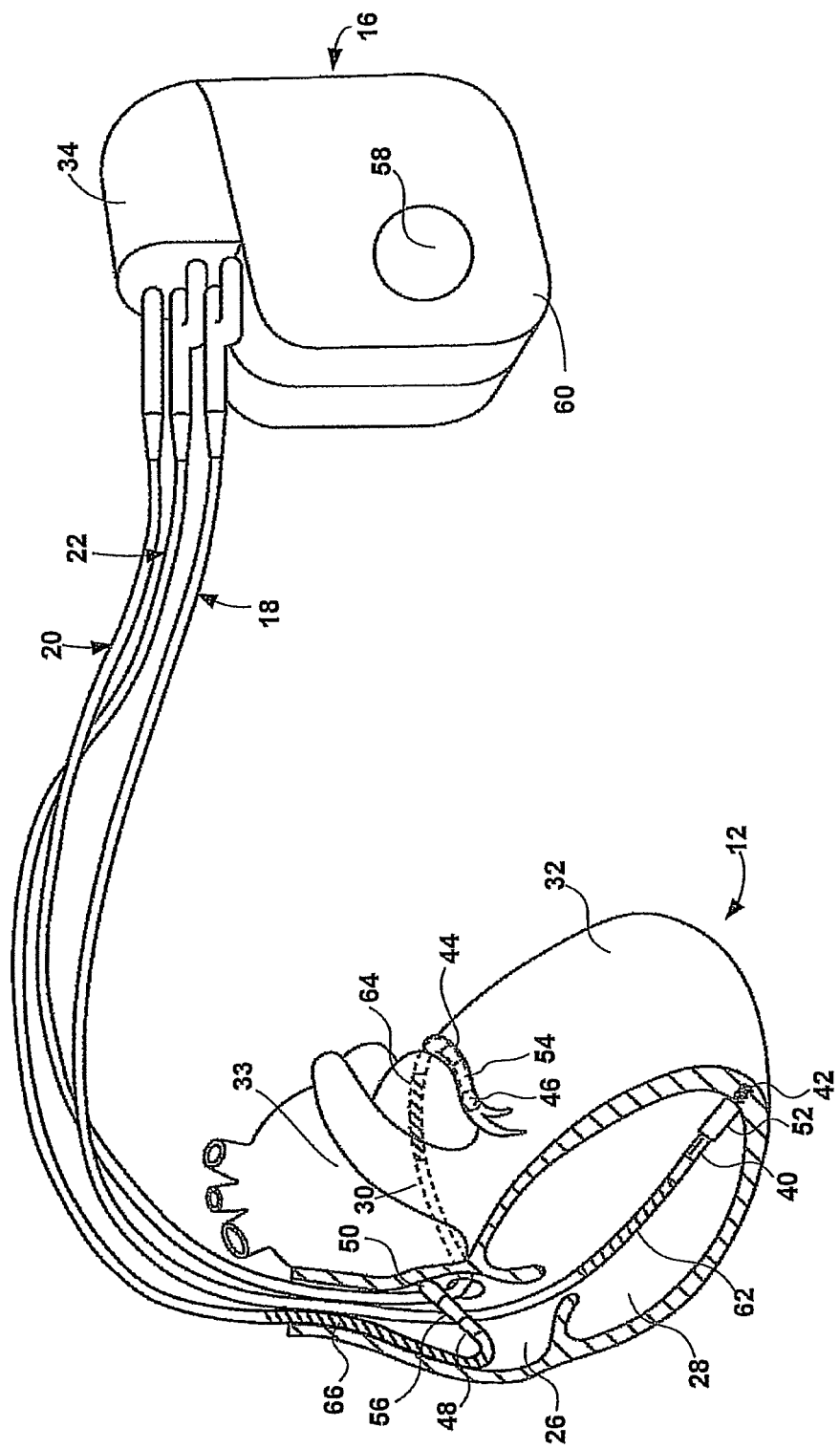
FIG. 2 is a diagram of the IMD of FIG. 1.

FIG. 2 is a conceptual diagram illustrating the IMD 16 and the leads 18, 20, 22 of the exemplary therapy system 10 of FIG. 1 in more detail. The leads 18, 20, 22 may be electrically coupled to a therapy delivery module, a sensing module, and/or any other modules of the IMD 16 via a connector block 34.

Each of the leads 18, 20, 22 includes an elongated insulative lead body, which may carry a number of concentric coiled conductors separated from one another by tubular insulative sheaths. In the illustrated example, bipolar electrodes 40, 42 are located proximate to a distal end of the lead 18. In addition, bipolar electrodes 44, 46 are located proximate to a distal end of the lead 20 and bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. In some examples, e.g., as illustrated in FIG. 2, the IMD 16 may include one or more housing electrodes, such as housing electrode 58, which may be formed integrally with an outer surface of a housing 60 (e.g., hermetically-sealed housing) of the IMD 16 or otherwise coupled to the housing 60.

The electrodes 40, 42, 44, 46, 48, 50, 58 and/or any other electrodes may further be used to sense impedance signals within the patient's heart 12. Impedance signals can be measured in a tissue segment (e.g., heart tissue segment) located in an electrode vector field between any two or more of the electrodes by injecting a current between two or more selected electrodes, measuring a voltage between two or more selected electrodes, and determining the impedance based on the injected current and the measured voltage. The impedance may change due to a change in the characteristics of the tissue in the electrode vector field (e.g., degradation of the cellular wall due to disease), due to a change in the distance between electrodes (e.g., the change in distance between the left ventricle and the right ventricle), and/or due to a change in blood volume contained with the electrode vector field.

For example, the IMD 16 may measure an impedance signal by injecting a current between electrode 40 and electrode 42 and measuring a voltage between electrode 42 and electrode 46. Further, for example, the IMD 16 may measure an impedance signal by injecting a current between electrode 42 and an electrode (not depicted) located in the right ventricle proximate the tricuspid valve and measuring a voltage between electrode 40 and the electrode (not depicted) located in the right ventricle proximate the tricuspid valve. Still further, for example, the IMD 16 may measure an impedance signal by injecting a current between electrode 50 and electrode 42 and measuring a voltage between electrode 48 and electrode 40. Yet still further, for example, the IMD 16 may measure an impedance signal by injecting a current between electrode 42 and electrode 58 and measuring a voltage between electrode 40 and electrode 58.

In essence, the exemplary methods and/or devices described herein may monitor one or more impedance vectors using one or more electrode configurations. Further, multiple impedance vectors may be measured concurrently and/or periodically with one another. In at least one embodiment, the exemplary methods and/or devices may switch between impedance vectors to find the most applicable fiducial points for a particular type of therapy to be delivered. For example, some impedance vectors may provide better data for optimizing CRT than others.

As used herein, the term "impedance signal" is not limited to a raw impedance signal. It should be implied that raw impedance signals may be processed, normalized, and/or filtered (e.g., to remove artifacts, noise, static, and/or extraneous signals) to provide the impedance signal. Further, the term "impedance signal" may include various mathematical derivatives thereof including real and imaginary portions of the impedance signal, a conductance signal based on the impedance (i.e., the reciprocal or inverse of impedance), etc. In other words, the term "impedance signal" may be understood to include conductance signals, i.e. signals that are the reciprocal of the impedance signal.

The leads 18, 20, 22 may also include elongated electrodes 62, 64, 66, respectively, which may take the form of a coil. The IMD 16 may deliver defibrillation shocks and/or cardioversion pulses to the heart 12 via any combination of the elongated electrodes 62, 64, 66, and the housing electrode 58.

The configuration of the exemplary therapy system 10 illustrated in FIGS. 1-2 is merely one example. In other examples, an exemplary therapy system may include epicardial leads and/or patch electrodes instead of or in addition to the transvenous leads 18, 20, 22 illustrated in FIGS. 1-2. Further, in one or more embodiments, the IMD 16 need not be implanted within the patient 14. For example, the IMD 16 may monitor impedance signals, deliver defibrillation shocks, and/or perform other therapies to the heart 12 via percutaneous leads that extend through the skin of the patient 14 to a variety of positions within or outside of the patient's heart 12.

In other exemplary therapy systems that provide electrical stimulation therapy to the heart 12, the therapy systems may include any suitable number of leads coupled to the IMD 16, and each of the leads may extend to any location within or proximate to the patient's heart 12. For example, other exemplary therapy systems may include three transvenous leads located as illustrated in FIGS. 1-2, and an additional lead located within or proximate to the left atrium 33. Still further, other exemplary therapy systems may include a lead that extends from the IMD 16 into the right atrium 26 or the right ventricle 28, two leads that extend into a respective one of the right ventricle 26 and the right atrium 28, and/or at least one lead that extends through the cardiac vein proximate the left atrium 33 and/or ventricle 32.

Figure 3:
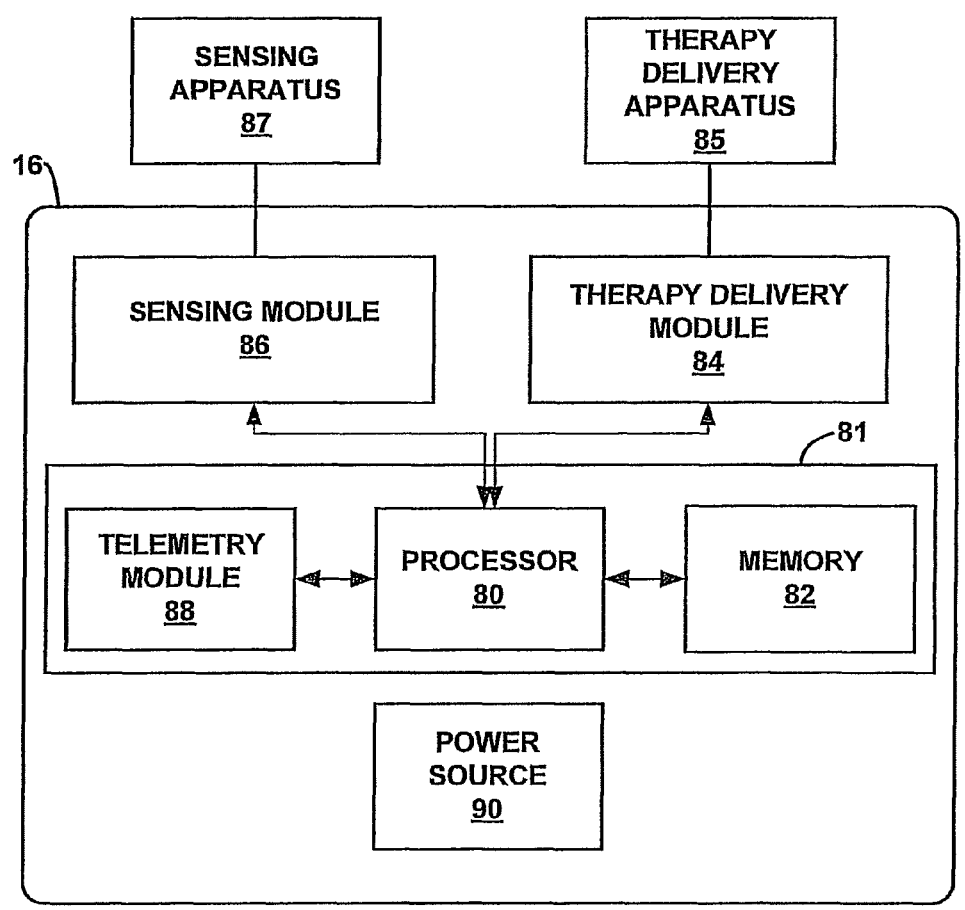
FIG. 3 is a block diagram of the IMD of FIG. 1.

FIG. 3 is a functional block diagram of one exemplary configuration of the IMD 16. As shown, the IMD 16 may include a control module 81, a therapy delivery module 84 (e.g., a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and the control module 81 to perform various functions attributed to the IMD 16 and the control module 81 described herein. Further, the memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The processor 80 of the control module 81 may include any one or more of a microprocessor, a controller, a digital signal processor (DSP), an application specific integrated circuit (ASIC), a field-programmable gate array (FPGA), or equivalent discrete or integrated logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the processor 80 herein may be embodied as software, firmware, hardware, or any combination thereof.

The control module 81 is coupled to and controls the therapy delivery module 84, which is configured to deliver therapy (e.g., electrical stimulation therapy) to the patient's heart 12 according to a selected one or more of therapy programs that may be stored in the memory 82. Specifically, the processor 80 of the control module 81 may control the therapy delivery module 84 to deliver electrical pulses with delays, timings, amplitudes, pulse widths, frequency, and/or electrode polarities specified by the selected one or more therapy programs (e.g., CRT programs, etc.).

The therapy delivery module 84 is coupled (e.g., electrically coupled) to therapy delivery apparatus 85 such that the therapy deliver module 84 may use the therapy delivery apparatus 85 to deliver therapy to the patient 14. The therapy deliver apparatus 85 may include, among other therapy delivery devices, the electrodes 40, 42, 44, 46, 48, 50, 58, 62, 64, 66 of the exemplary system of FIGS. 1-2 (e.g., via conductors of the respective leads 18, 20, 22). The therapy delivery module 84 may be configured to generate and deliver electrical stimulation therapy to the heart 12. For example, the therapy delivery module 84 may deliver pacing pulses (e.g., for use in providing CRT) via the ring electrodes 40, 44, 48 coupled to the leads 18, 20, 22, respectively, and/or the helical electrodes 42, 46, 50 of the leads 18, 20, 22, respectively. Further, for example, the therapy deliver module 84 may deliver defibrillation shocks to the heart 12 via at least two of the plurality of electrodes, e.g., electrodes 58, 62, 64, 66. In some examples, the therapy delivery module 84 may deliver pacing, cardioversion, and/or defibrillation stimulation in the form of electrical pulses.

The control module 81 is coupled to and controls the sensing module 86 to receive one or more signals from sensing apparatus 87. The sensing module 86 is coupled (e.g., electrically coupled) to sensing apparatus 87, e.g., to monitors signals from the sensing apparatus 87. The sensing apparatus 87 may include the electrodes 40, 42, 44, 46, 48, 50, 58, 62, 64, 66 to monitor electrical activity of the heart 12, e.g., impedance signals between two or more electrodes, electrocardiogram (ECG) signals, etc. The sensing apparatus 87 may further include one or more pressure sensors, posture sensors (e.g., accelerometers), heart sound sensors, etc.

As described herein, the IMD 16 may be configured to generate and deliver electrical stimulation (e.g., pacing pulses) to the patient's heart 12, and as such, the control module 81 may include a pacer timing and control module, which may be embodied as hardware, firmware, software, or any combination thereof. The pacer timing and control module may comprise a dedicated hardware circuit, such as an ASIC, separate from the other components, such as a microprocessor, or an executable software module. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module may include the AV delay, the VV delay, etc. The AV delay may be defined as the time interval between pacing the atria and pacing the ventricles of the patient's heart 12 and the VV delay may be defined as the time interval between pacing the left ventricle and the pacing the right ventricle of the patient's heart 12. The durations of these intervals may be determined by the processor 80 of the control module 81 in response to stored values in the memory 82 (e.g., nominal AV and/or VV delays, clinician selected AV and/or VV delays, automatically-adjusted AV and/or VV delays such as those, for example, based on impedance signals, etc.). As used herein, values described as "nominal" (e.g., such as nominal AV or VV delays) may be default values that are preset within the IMD 16 or set by a clinician. In other words, nominal values may be initial or start values that, e.g., may be adjusted in the future.

The therapy delivery module 84 may include pacer output circuits that are selectively coupled (e.g., using switching circuitry) to any one or more of the electrodes 40, 42, 44, 46, 48, 50, 58, 62, 66 appropriate for delivery of a bipolar or unipolar pacing pulse to one of the portions of the patient's heart 12.

The telemetry module 88 of the control module 81 may include any suitable hardware, firmware, software, or any combination thereof for communicating with another device, such as the programmer 24 (FIG. 1). For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88. Further, the telemetry module 88 may provide received data to the processor 80 via a multiplexer.

In at least one embodiment, the control module 81 may transmit impedance signal data (e.g., produced by using various electrodes proximate the patient's heart 12) using the telemetry module 88 to an external device, such as the programmer 24, such that a clinician and/or patient may view the impedance signal data. The impedance signal data may be further processed or filtered such that the impedance signal data includes a signal that represents various mechanical cardiac events as described herein (e.g., E-wave portions and A-wave portions representative of E-waves and A-waves of a cardiac cycle). In other words, the IMD 16 may transmit data representative of mechanical cardiac events based on the impedance signal data to an external device such that a clinician may use the data for diagnostic purposes, therapy adjustment (e.g., CRT adjustment), etc.

In at least one embodiment, the transmitted data may include E-waves and A-waves, representative of blood flow velocity across the mitral valve of the patient's heart 12. A clinician may use a device, e.g., the programmer 24, to interrogate the IMD 16 to receive such impedance-based E-wave portions and A-wave portions (e.g., E-wave portions and A-wave portions of an impedance signal or derivative thereof) to evaluate the patient's hemodynamic function and to program the IMD 16 based on such evaluation. For example, a clinician may use transmitted data including the impedance-based E-wave and A-wave portions from the IMD 16 to optimize CRT provided by the IMD 16 (e.g., modifying or adjusting the AV and/or VV delays).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

The methods and/or devices described herein may monitor various impedance signals between two or more electrodes proximate a patient's heart and/or deliver therapy to the patient's heart based on those various impedance signals. Exemplary generalized methods 200, 400 for use in monitoring a patient's heart and/or delivering cardiac therapy are diagrammatically depicted in FIG. 4 and FIG. 10. Methods 200, 400 are intended to illustrate the general functional operation of the devices and/or systems described herein, and should not be construed as reflective of a specific form of software or hardware necessary to practice all of the methods described herein. It is believed that the particular form of software will be determined primarily by the particular system architecture employed in the device (e.g., the IMD 16) and by the particular detection and therapy delivery methodologies employed by the device and/or system. Providing software and/or hardware to accomplish the described methods in the context of any modern IMD, given the disclosure herein, is within the abilities of one of skill in the art.

Figure 4:
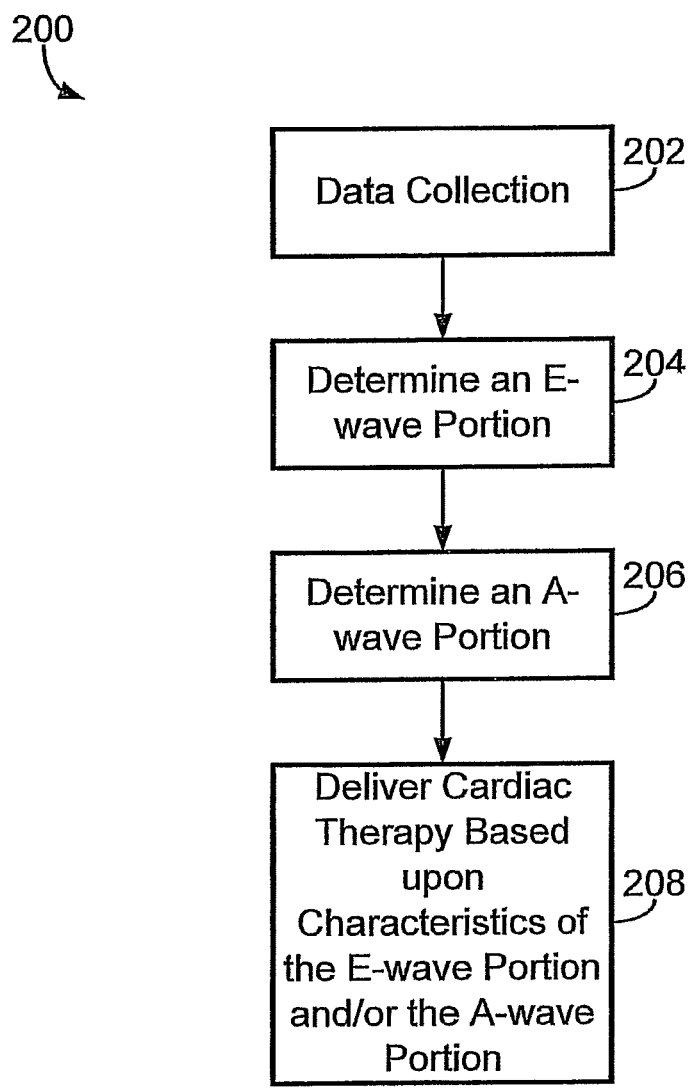
FIG. 4 is a flow chart of an exemplary method for use in delivering therapy to a patient's heart, e.g., using the IMD of FIGS. 1-3.

The method 200 of FIG. 4 includes a data collection process (block 202). The data collection process (block 202) may include monitoring an impedance between at least two electrodes proximate the patient's heart to provide an impedance signal. The at least two electrodes may be located within or proximate various locations of the patients heart (e.g., as described herein with reference to FIGS. 1-2). In at least one embodiment, an impedance signal may be monitored by injecting a current between an electrode located proximate (e.g., on) the left ventricle (LV) epicardial surface and an electrode located in the right ventricle (RV) and measuring a voltage between an electrode located proximate (e.g., on) the LV epicardial surface and an electrode located in the RV. In at least another embodiment, an impedance signal may be monitored by injecting a current between an electrode located in the RV and an electrode located in the right atrium and measuring a voltage between an electrode located in the RV and an electrode located in the right atrium. In at least still another embodiment, an impedance signal may be monitored using a tripolar configuration, e.g., by injecting a current between a coil electrode located in the RV and a tip electrode in the RV and measuring a voltage between a ring electrode located in the RV and the tip electrode in the RV. Further, in one or more embodiments, a housing electrode may be used to inject a current or monitor a voltage in conjunction with another electrode, e.g., located in the right ventricle.

Although not described in detail herein, the impedance signal may be processed and/or filtered using various algorithms as known in the art to remove artifacts, noise, static, and/or extraneous signals (e.g., respiratory components, etc.) from the impedance signal. Exemplary processing and filtering techniques may be described in U.S. App. Pub. No 2009/0275854 A1 to Zielinski et al., which is included herein by reference in its entirety.

The method 200 may further include determining an E-wave portion (block 204) representative of an E-wave during a cardiac cycle based on the impedance signal. An E-wave is a wave that is observable by a clinician using echocardiography of the mitral valve of a patient's heart and may represent the blood flow velocity across the mitral valve during left ventricular diastole after the mitral valve opens (also known as the early diastolic filling phase). Generally, about 80% of the blood that travels across the mitral valve occurs during this early diastolic filling phase.

As used herein, the E-wave portion may be based on the impedance signal or derivative thereof, a conductance signal based on the impedance signal or derivative thereof, or any other signal or data based on the impedance signal that corresponds to or represents the E-wave that is representative of blood flow velocity across the mitral valve during the early diastolic filling phase.

Although an arrow is shown in FIG. 4 extending from the data collection process (block 202) to E-wave portion determination (block 204), the data collection process (block 202) and the E-wave portion determination (block 204), as well as other processes described herein, may be executed concurrently as opposed to sequentially or periodically.

Similar to determining the E-wave portion (block 204), the method 200 further includes determining an A-wave portion (block 206) representative of an A-wave during a cardiac cycle based on the impedance signal. An A-wave is also a wave that is observable by a clinician using echocardiography of the mitral valve and may represent blood flow velocity across the mitral valve during left atrial contraction, or left atrial systole/left ventricular diastole, but prior to left ventricular systole (also known as a late or active diastolic filling phase or atrial kick). About 20% of the blood that travels across the mitral valve occurs during this late diastolic filling phase.

As used herein, the A-wave portion may be based on the impedance signal or derivative thereof, a conductance signal based on the impedance signal or derivative thereof, or any other signal or data based on the impedance signal that corresponds to or represents the A-wave that is representative of blood flow velocity across the mitral valve during the late diastolic filling phase.

Figure 5:
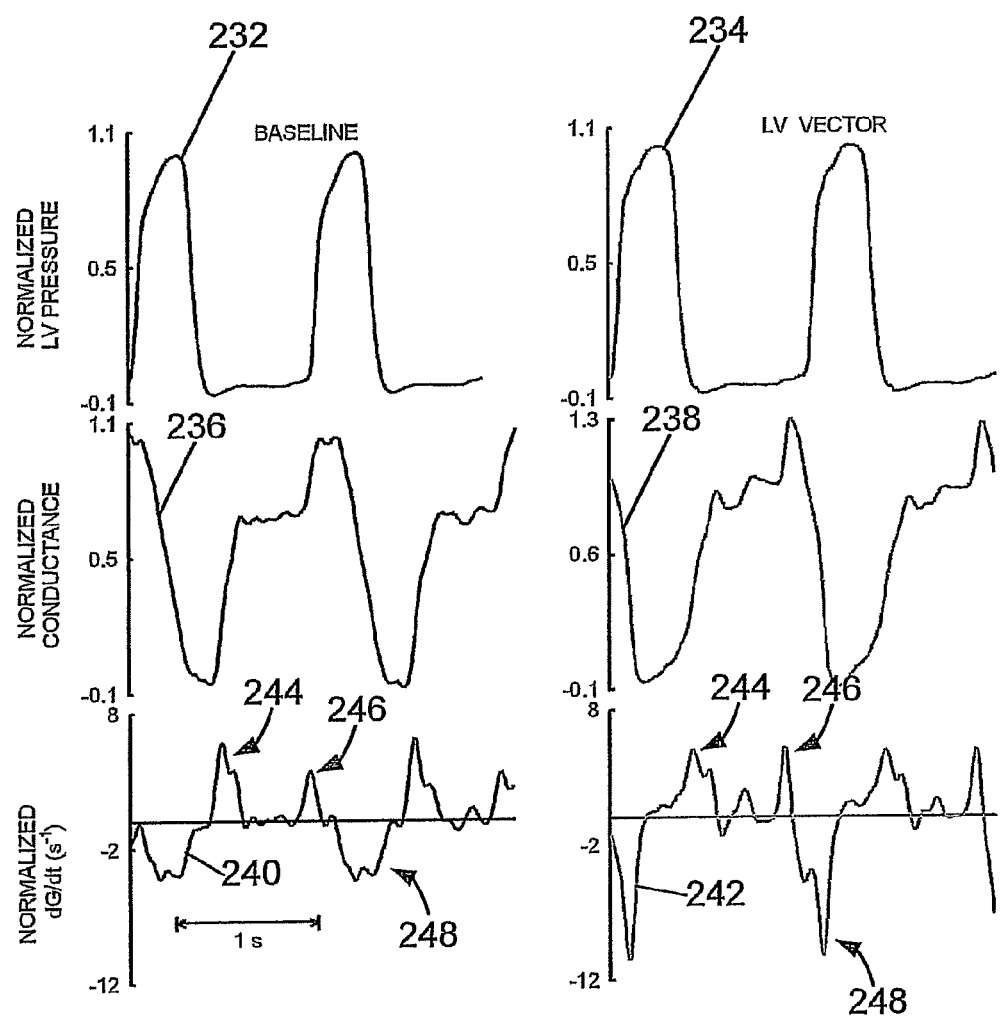
FIG. 5 includes exemplary graphical depictions of various parameters associated with a patient's heart plotted over a time period.

For example, E-wave and A-wave portions based on impedance signals or derivatives thereof are depicted in FIG. 5. Generally, three parameters, namely left ventricular pressure signals 232, 234 (provided for reference), normalized conductance signals 236, 238 (i.e., the inverse or reciprocal of impedance), and the first derivative of the normalized conductance signals 240, 242, are plotted over time in FIG. 5. The conductance signal 236 and the derivative conductance signal 240 were measured using a standard or baseline conductance catheter technique; the conductance signal 238 and the derivative conductance signal 242 were measured using a simulated pacemaker left ventricle vector configuration. In the simulated pacemaker LV vector configuration, current was driven between one pair of electrodes located proximate (e.g., on) the LV epicardial surface within a branch of the coronary sinus and the right ventricular apex, respectively. The resultant voltage, and hence impedance, was simultaneously measured from an adjacent pair of electrodes located in the same regions. Although the impedance signal in this example is captured using a specific electrode vector configuration, impedance signals or derivatives thereof may be captured using one or more different electrode vector configurations as described herein and may also be used to provide E-wave and A-wave portions.

As shown, conductance may be proportional to left ventricle volume, and as such, the derivative of the conductance signals 236, 238 may be proportional to mitral flow (e.g., blood flow velocity across the mitral valve during filling) and aortic flow (e.g., blood flow velocity across the aortic valve during ejection).

The E-wave portions 244 and A-wave portions 246 are identified in the derivative conductance signals 238, 242 of FIG. 5. Further, the negative portions 248 of the derivative conductance signals 240, 242 are also identified and may be representative of or proportionate to aortic ejection velocity, similar to commonly-measured aortic velocity (VTI) measurements.

Although the E-wave portions 244 and A-wave portions 246 are indicated in the derivative signals 240, 242, the E-wave and A-wave portions may also be identified in a non-derivative and/or raw normalized conductance signal (e.g., an impedance signal). For example, as described herein, E-wave and A-wave portions are identified in an impedance signal in FIG. 6.

Figure 6:
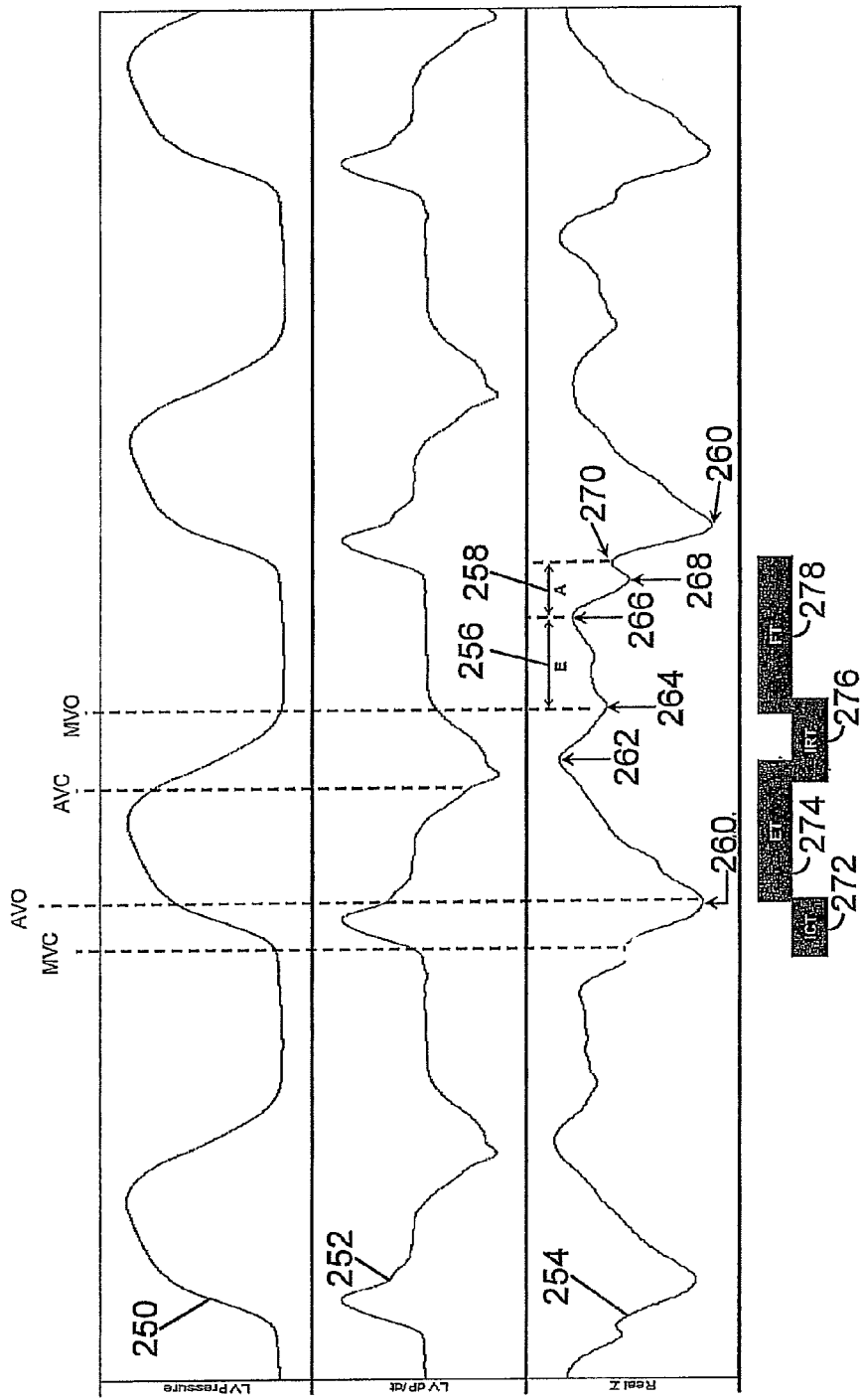
FIG. 6 includes more exemplary graphical depictions of various parameters associated with a patient's heart plotted over a time period.

A left ventricular pressure signal 250, a first derivative of the left ventricular pressure signal 252, and an impedance signal 254 are plotted over time in FIG. 6. As shown, an E-wave portion 256 and an A-wave portion 258 have been determined and identified based on (e.g., within) the impedance signal 254.

The E-wave and A-wave portions 244, 256, 246, 258 shown in FIGS. 5-6 may be determined based on an impedance signal using various techniques. For example, an impedance signal or derivative thereof may be analyzed for various landmarks or signatures such that one or more fiducial points (e.g., local maxima and minima) associated with the E-wave and A-wave portions 256, 258 may be identified. As used herein, a fiducial point may be defined as a single point or a portion (e.g., a plurality of points, a waveform segment, etc.) of a signal or derivative thereof. For example, a fiducial point may be a maximum value, a minimum valve, a wave portion, etc.

Determination of fiducial points may be made using any known techniques from the impedance signal alone, or from a combination of an impedance signal and an additional signal. For example, an electrogram signal of the patient's heart may be simultaneously measured by implantable devices. The electrogram signal contains the components of a standard cardiac electrocardiogram signal, including P-waves, R-waves, T-waves, QRS complexes, etc. that are associated temporally with specific mechanical events of the cardiac cycle. For example, the electrogram signal may be used to identify a time period immediately after the QRS complex when early filling (e.g., an E wave) was likely to occur, and specific methods may be used to identify fiducial points of the conductance signal within such an electrogram-identified time period in order to identify the timing of the E-wave with greater accuracy.

A plurality of fiducial points may be identified within the impedance signal 254, as shown in FIG. 6, that correspond to various mechanical cardiac events. As such, one or more characteristics of various mechanical cardiac events may be determined using one or more of the plurality of fiducial points.

For example, fiducial point 260 is the minimum value of the impedance signal 254 and may correspond to the opening of the aortic valve and the start of the ejection time period 274. Fiducial point 262 is the first peak following the fiducial point 260 (i.e., the minimum value) and in this case, is the maximum for this cardiac cycle. Further, fiducial point 262 may correspond to the closing of the aortic valve and the end of the ejection time period 274. As a result, the fiducial points 260, 262 identified on the impedance waveform 254 may be used to estimate the ejection time period 274.

Further, for example, fiducial point 264 is the first trough, or low point, following the fiducial point 262 and may correspond to the opening of the mitral valve, the start of the filling time period 278, and the start of the E-wave portion 256. As such, the fiducial points 262, 264 may be used to estimate the isovolumetric relaxation period. Fiducial point 266 is the first peak following the fiducial point 264 and may correspond to the slow filling period of the ventricle (e.g., after the early filling phase but before atrial contraction and the late filling phase) and the start of the atrial contraction (e.g., atrial kick) or A-wave portion 258. As such, the fiducial points 264, 266 may be used to estimate the time period of the E-wave portion.

Still further, fiducial point 268 is the first trough, or low point, following the fiducial point 266 and may correspond to peak atrial contraction. Fiducial point 270 is the first peak following the fiducial point 268 and may correspond to the beginning of left ventricular contraction, the end of diastole, mitral valve closure, and therefore, the end of both the filling time period 278 and the A-wave portion 258. As such, the fiducial points 266, 270 may be used to estimate the time period of the A-wave portion 258 and the fiducial points 264, 270 may be used to estimate the filling time period 278.

Generally, impedance values at various fiducial points, time interval between various fiducial points, areas under the curve between various fiducial points, slopes between or at various fiducial points, integrals between various fiducial points, etc. may be identified and/or measured in order to determine various segments of the cardiac cycle such as, e.g., the isovolumetric contraction time 272, ejection time period 274, isovolumetric relaxation time 276, filling time period 278, etc.

With further reference to FIG. 4, the method 200 may further include delivering cardiac therapy (block 208) to the patient based upon one or more characteristics associated with at least one of the E-wave portion 244, 256 and the A-wave portion 246, 258. The one or more characteristics associated with the E-wave portions 244, 256 and the A-wave portions 246, 258 of the impedance signal or derivative thereof may correspond to one or more characteristics of actual E-waves and A-waves representative of blood flow velocity across the mitral valve (e.g., observable using an echocardiograph of the mitral valve). By analyzing the one or more characteristics associated with the E-wave portions 244, 256 and the A-wave portions 246, 258, the method 200 may determine one or more parameters at which the cardiac therapy should be delivered, e.g., AV delay, VV delay, etc. Further, analysis of the one or more characteristics associated with the E-wave portions 244, 256 and the A-wave portions 246, 258 not need result in the delivery of therapy. For example, the one or more characteristics associated with the E-wave portions 244, 256 and the A-wave portions 246, 258 and/or the E-wave portions 244, 256 and the A-wave portions 246, 258 themselves may be used for monitoring purposes (e.g., diagnostic purposes, manual adjustment of therapy parameters by a clinician, etc.).

Figure 7:
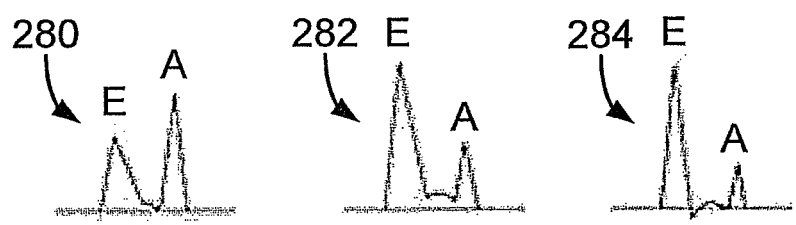
FIG. 7 includes exemplary graphical depictions of blood flow velocity across the mitral valve of a patient's heart over a time period.

For example, exemplary E-waves and A-waves are depicted in FIG. 7. The first E-A waveform 280 may be indicative of impaired relaxation of the left ventricle, the second E-A waveform 282 may be indicative of proper heart function, and the third E-A waveform 284 may be indicative of restrictive mitral valve functionality. Characteristics of the first E-A waveform 280 may include a peak of the E-wave that less than the peak of the A-wave, a longer than normal E-wave interval, a larger than normal A-wave amplitude, a lower ratio of the peak E-wave amplitude to A-wave amplitude, a lower ratio of the areas under the respective A-wave and E-wave curves, etc. Characteristics of the second E-A waveform 282 may include an E-wave peak that is greater than the A-wave peak, a trough value located between the E-wave peak and the A-wave peak that is greater in duration than a selected time period, etc. Characteristics of the third E-A waveform 284 may include a shorter than normal E-wave interval, a truncated A-wave interval, potentially a reversal in flow values (e.g., negative values), etc.

Furthermore, timing intervals between fiducial points on the E- and A-waves may correspond to typical parameters derived from echocardiography. For example, a time interval from the start of the E-wave (e.g., minimum value) to the E-wave peak (e.g., maximum value) may represent time to ejection velocity. Further, for example, a time interval from the E-wave peak to the following E-wave minimum (prior to the A-wave) may represent the deceleration time, and the slope associated with this timing interval represents the early diastolic deceleration slope.

The method 200 may compare one or more characteristics of the determined E-wave and A-wave portions (block 208) of the impedance signal or derivative thereof to one or more characteristics associated with actual E-A waveforms that are indicative of healthy, unhealthy, normal, and/or abnormal heart function (e.g., hemodynamic function). Such comparisons may be used to determine various parameters (e.g., AV delay, VV delay, etc.) of the cardiac therapy. In other words, delivering cardiac therapy (block 208) to the patient may be based upon one or more characteristics associated with at least one of the E-wave portion 244, 256 and the A-wave portion 246, 258.

Figure 8:
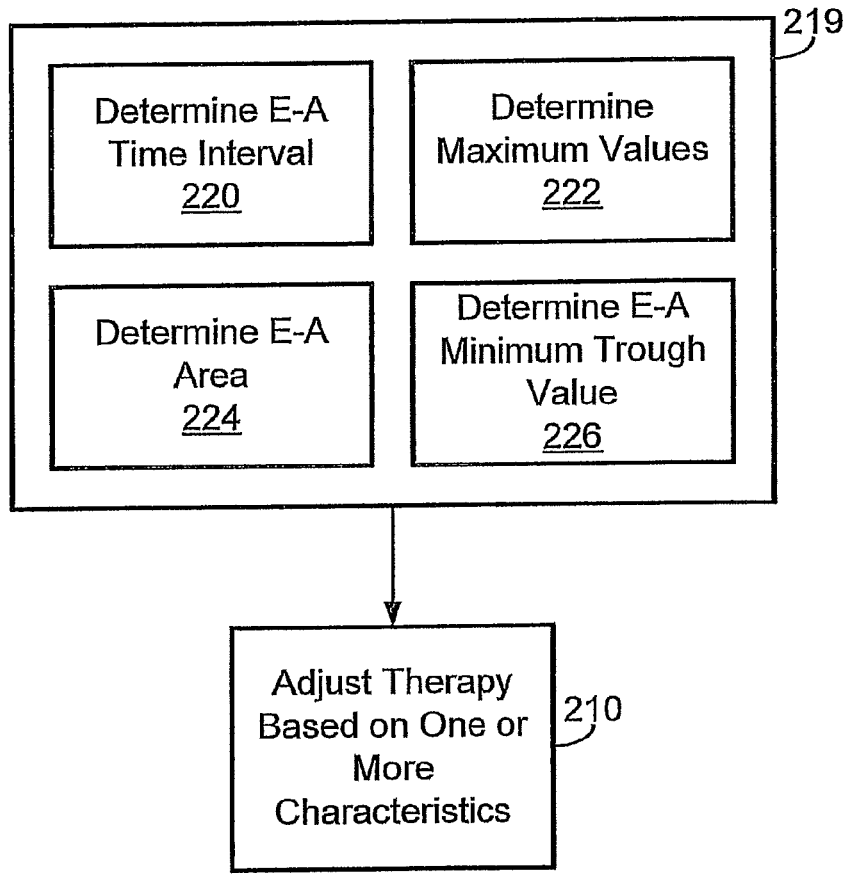
FIG. 8 is a flow diagram of an exemplary method to be used in conjunction with the method of FIG. 4.

As shown in FIG. 8, various determinations 219 may be executed to deliver cardiac therapy (block 208) to the patient based upon one or more characteristics associated with at least one of the E-wave portion 244, 256. For example, an E-A time interval between selected points (e.g., the peak, the start, the end, etc.) based on (e.g., within) each of the E-wave and A-wave portions may be determined (block 220) and used to deliver cardiac therapy to the patient (block 210). The E-A time interval may be compared to one or more selected values indicative of healthy, unhealthy, normal, and/or abnormal heart function to determine whether cardiac therapy should be delivered or whether presently-delivered cardiac therapy should be adjust or terminated. In at least one embodiment, the AV delay may be progressively decreased in order to maximize the time interval between the E-wave and the A-wave but without compromising the area under the A-wave curve. A decrease in the area under the A-wave curve at a given AV interval compared to a longer time interval between the E-wave and the A-wave could imply truncation of the atrial contraction by LV contraction. Further, truncation of the A-wave may limit ventricular filling and hence LV preload.

Further, for example, a maximum value, or peak value, of the E-wave portion, a maximum value, or peak value, of the A-wave portion (e.g., of the impedance signal or derivative thereof, of the first derivative of the conductance signal, etc.) and/or the ratio between the maximum values of the E-wave portion and the A-wave portion may be determined (block 222) and used to deliver cardiac therapy to the patient (block 210). The maximum values of the E-wave and A-wave portions and/or the ratio between the maximum values may be compared to one or more selected values indicative of healthy, unhealthy, normal, and/or abnormal heart function to determine whether cardiac therapy should be delivered or whether presently-delivered cardiac therapy should be adjust or terminated. In at least one embodiment, the AV delay may increased or decreased in order to maximize the ratio between the maximum values of the E-wave portion and the A-wave portion.

Still further, for example, an E-A area under, an E-wave portion (E-wave area), an A-wave portion (A-wave area), or both the E-wave portion and the A-wave portion (E-A wave area), and/or a ratio between the area under an E-wave portion and the area under an A-wave portion (E-A area ratio) (e.g., in the first derivative of the conductance signal) may be determined (block 224) and used to deliver cardiac therapy to the patient (block 210). The E-wave area and the A-wave area may be representative of the early and late fill volumes of the left ventricle, respectively. These early and late filling volumes may also be directly determined from the raw conductance signals (e.g., the change in amplitude from the time of mitral valve opening to the time of atrial contraction may correlate to early filling volume, the change in amplitude from the time of atrial contraction to the time of ventricular contraction may correlate to late filling volume). The E-wave area, A-wave area, E-A wave area, and/or the E-A area ratio may be compared to one or more selected values indicative of healthy, unhealthy, normal, and/or abnormal heart function to determine whether cardiac therapy should be delivered or whether presently-delivered cardiac therapy should be adjust or terminated. In at least one embodiment, the AV delay could be increased or decreased until the E-A area ratio was at a maximum value.

Yet still further, for example, an E-A minimum trough value (e.g., of the first derivative of the conductance signal) between the E-wave portion and A-wave portion maximum values may be determined (block 226) and used to deliver cardiac therapy delivered to the patient (block 210). The E-A minimum trough value may correspond to the blood flow during the slow filling of the ventricle, a period known as diastasis. The E-A minimum trough value may be compared to one or more selected values indicative of healthy, unhealthy, normal, and/or abnormal heart function to determine whether cardiac therapy should be delivered or whether presently-delivered cardiac therapy should be adjust or terminated. In at least one embodiment, the AV delay could be adjusted so as to minimize the amplitude of the E-A minimum trough value but maintain an area under the A-wave portion. In effect, both early and late filling may be maximized, but atrial contraction may not be truncated by the onset of ventricular contraction.

In another embodiment, the deceleration time of the E-wave negative slope may be obtained by extrapolating the time of the decay of the E-wave velocity (e.g., the maximum point) to a baseline value (e.g., the minimum point at start of diastasis) and may be used during CRT optimization to improve the passive inflow pattern by maximizing E-wave height and width and reducing the deceleration time.

Figure 9:
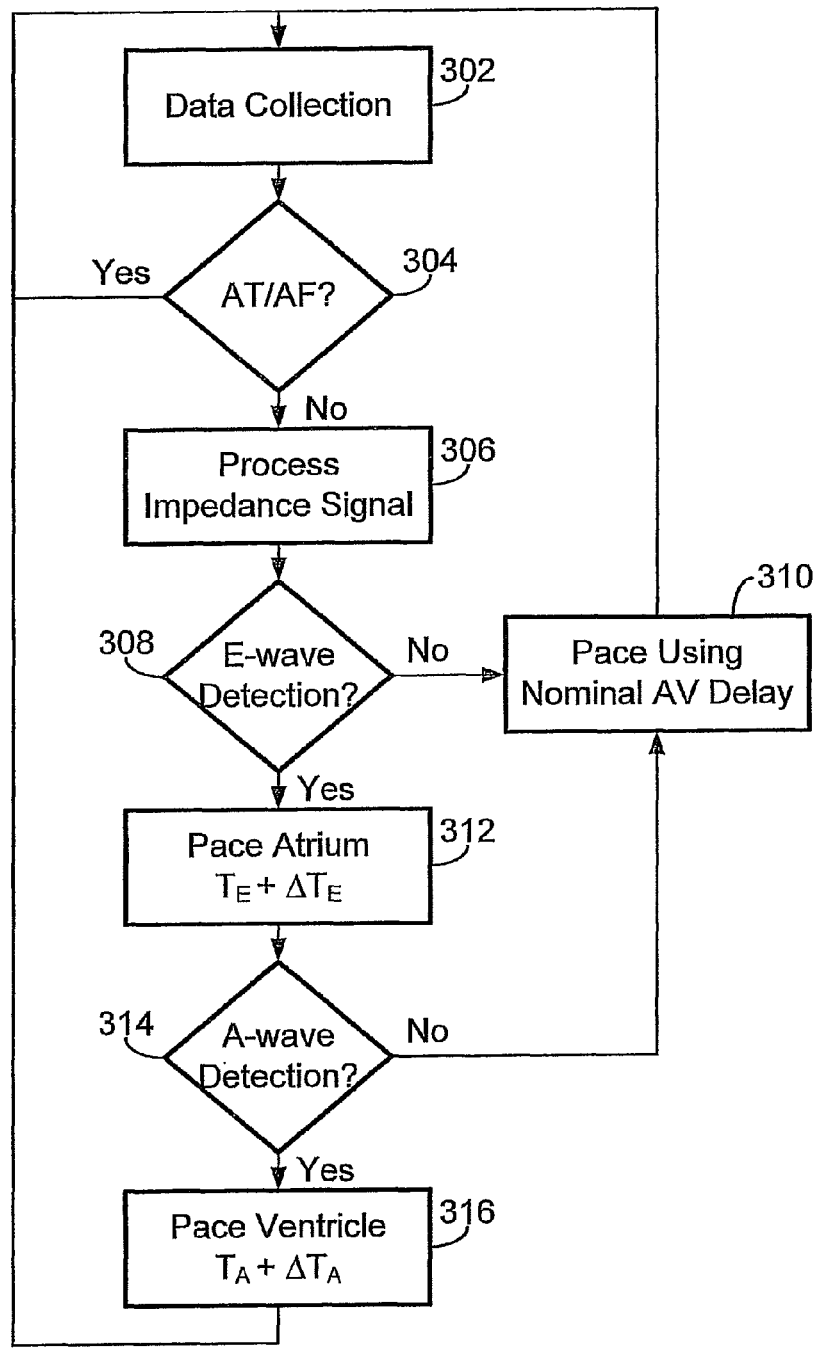
FIG. 9 is a flow chart of another exemplary method for use in delivering therapy to a patient's heart, e.g., using the IMD of FIGS. 1-3.

An exemplary method 300 for use in delivering cardiac therapy to a patient is depicted in FIG. 9. More specifically, the method 300 provides a method for adjusting CRT parameters such as AV delay and VV delay.

The method 300 may include a data collection process (block 302). The data collection process (block 302) may include monitoring one or more physiological parameters and may be similar to the data collection process (block 202) described herein with reference to FIG. 4. Such physiological parameters may include impedance signals, ECG signals, etc.

Although not depicted, the method 300 may be triggered or initiated by various triggering events such as, e.g., an acute change in activity, an acute change in heart rate, a posture change (e.g., detected using an accelerometer), a termination of an atrial or ventricular tachyarrhythmia, an acute change in a conducted AV delay or heart rate variability, etc. Further, in at least one embodiment, the method 300 may be initiated manually by a clinician or patient using the programmer 24 or any other remote device.

If a patient's heart is undergoing atrial tachycardia or atrial fibrillation, the method 300 may not be desired. For example, as shown, if atrial tachycardia or atrial fibrillation is detected (block 304), the method 300 may not proceed. If atrial tachycardia or atrial fibrillation is not detected (block 304), the method 300 may progress to processing an impedance signal (block 306). For example, during atrial fibrillation, the atrium may not actively contract such that an A-wave may not be detected, and therefore, the atrium may not need to be paced. Further, the absence of an A-wave (based on the impedance signal) may be useful as a diagnostic sensing mechanism for atrial fibrillation.

In at least one embodiment, if one or more certain fiducial points are not detected, the method may switch to a different electrode vector configuration (e.g., injecting a current between a different combination of two electrodes, monitoring a voltage between a different combination of two electrodes, etc.). For example, if an A-wave was not detected, the method may switch to a different vector configuration. If the A-wave is still not detected after switching to a different electrode vector configuration, the method may switch to yet another different electrode vector configuration or determine that the patient is undergoing atrial fibrillation. Further, sampling an ancillary signal such as, e.g., an ECG waveform, may aid in atrial fibrillation detection and validation.

The impedance signal may be processed (block 306) (e.g., normalized, denoised, etc.) to provide a signal such that E-wave and A-wave portions may be detected using various signal processing techniques (e.g., determining a derivative signal thereof). After the signal has been processed (block 306), the method 300 may progress to detecting an E-wave portion (block 308) based on the impedance signal. If an E-wave portion is not detected (block 308), the method 300 may not adjust the present nominal CRT parameters and may pace the patient's heart at nominal CRT parameters (block 310) (e.g., nominal AV and VV delays, default parameters, etc.).

If an E-wave portion is detected (block 308) based on the impedance signal, the method 300 may pace the atrium (block 312) after a first selected time period (delta $T_E$) after the time ($T_E$) at which a selected point in the E-wave portion (e.g., the peak or maximum value, the start of the E-wave portion, the end of the E-wave portion, etc.) occurs.

If an A-wave portion is detected (block 314), the method 300 may pace the ventricle (block 316) after a second selected time period (delta $T_A$) after the time ($T_A$) at which a selected point in the A-wave portion (e.g., the peak or maximum value, the start of the A-wave portion, the end of the A-wave portion, etc.) occurs. The selected time period (delta $T_A$) may also be referred to as the AV delay. Further, the delta $T_E$ and the delta $T_A$ may vary depending on a patient's age and/or various factors relating to the health of the patient.

The method 300 may be used either periodically or continuously, and although not depicted, the first and second selected time periods (e.g., delta $T_E$ and delta $T_A$) may be stored using the method 300 so that they may be used in the future. In at least one embodiment, the method 300 may continuously operate such that the CRT parameters may be adjusted continuously. In at least another embodiment, the method 300 may operate once a day to re-adjust the CRT parameters. In at least another embodiment, the method 300 may be clinician or patient triggered to adjust or re-adjust the CRT parameters.

In at least another embodiment, atrial and ventricular pacing timings may be based on electrically determined events (e.g., atrial activation, ventricular activation, etc.), and such atrial and/or ventricular pacing timings may be adjusted relative to these electrical events based on determinations using one or more fiducial points (e.g., each associated with a mechanical cardiac event) based on cardiac tissue impedance. The time period from an atrial event to a paced ventricular event (e.g., AV delay) may be in the range of about 60 milliseconds (ms) to about 200 ms (e.g., 150 ms) and the time period between a sensed or paced ventricular event and the paced or sensed bi-ventricular pace (e.g., VV delay) may be about 0 ms to about 100 ms (e.g., 0 ms to about 10 ms) (e.g., the bi-ventricular pace may be initiated in either ventricle). Such time periods may be adjusted (e.g., increased or decreased) by a selected value (e.g., 5 ms, 10 ms, 20 ms, 30 ms, etc.) based on determinations using one or more fiducial points. For example, the AV and/or VV delay based on electrically determined events may be adjusted to maximize the duration between the E-wave and the A-wave without decreasing the area under the A-wave (e.g., truncation caused by ventricular contraction). In other words, one or more of the methods described herein with respect to delivering and/or adjusting therapy in response to one or more fiducial points based on a cardiac impedance signal may be used in conjunction with (e.g., to enhance) closed-loop AV delay optimization methods based on electrically determined events.

As described with reference to FIG. 6, one or more fiducial points other than the points associated with the E-wave and A-wave portions may be determined or identified based on an impedance signal between two or more electrodes located proximate a patient's heart, e.g., acquired from one or more electrode vector configurations. Cardiac therapy may also be delivered based on the one or more fiducial points other than the points associated with the E-wave and A-wave portions.

Figure 10:
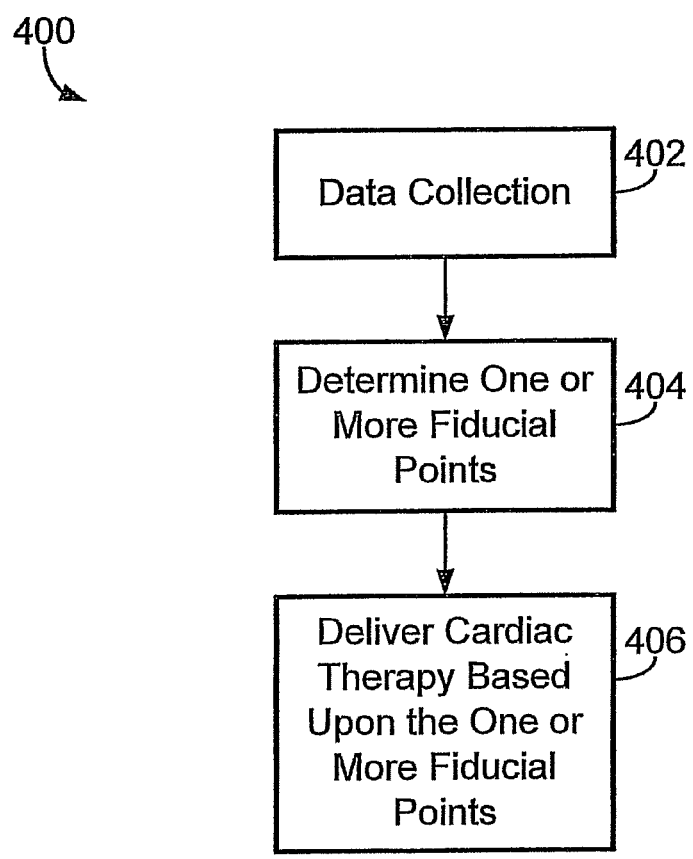
FIG. 10 is a flow chart of another exemplary method for use in delivering therapy to a patient's heart, e.g., using the IMD of FIGS. 1-3.

An exemplary generalized method 400 for use in delivering therapy to a patient's heart using one or more fiducial points is diagrammatically depicted in FIG. 10. The method 400 includes a data collection process (block 402) that is similar to the data collection process (block 202) described herein with reference to FIG. 4. The data collection process (block 402) may monitor and provide various physiological parameters of the patient including at least a cardiac impedance signal.

One or more fiducial points (e.g., as depicted in FIG. 6) may be determined (block 404) based on the impedance signal (or derivative thereof) acquired in the data collection process (block 402). Each fiducial point may be associated with a different mechanical cardiac event during a cardiac cycle. For example, a different fiducial point may be associated with aortic valve opening, aortic valve closing, mitral valve opening, mitral valve closing, atrium contraction, ventricle contraction, ejection time, filling time, E-wave, A-wave, isovolumetric contraction time, isovolumetric relaxation time, stroke volume, rapid filling, atrial systole, aortic flow wave, mitral regurgitation volume, early LV and/or RV filling volume, diastolic filing and/emptying, etc.

As such, the method 400 may use one or more fiducial points to deliver cardiac therapy based upon at least one fiducial point or one or more characteristics associated with the one or more fiducial points (block 406).

The method 400 may compare at least two fiducial points or one or more characteristics associated with one or more fiducial points to one or more characteristics or values that are indicative of healthy, unhealthy, normal, and/or abnormal heart function (e.g., hemodynamic function). Such comparisons may be used to determine various parameters (e.g., AV delay, VV delay, indices, etc.) of the cardiac therapy.

Figure 11:
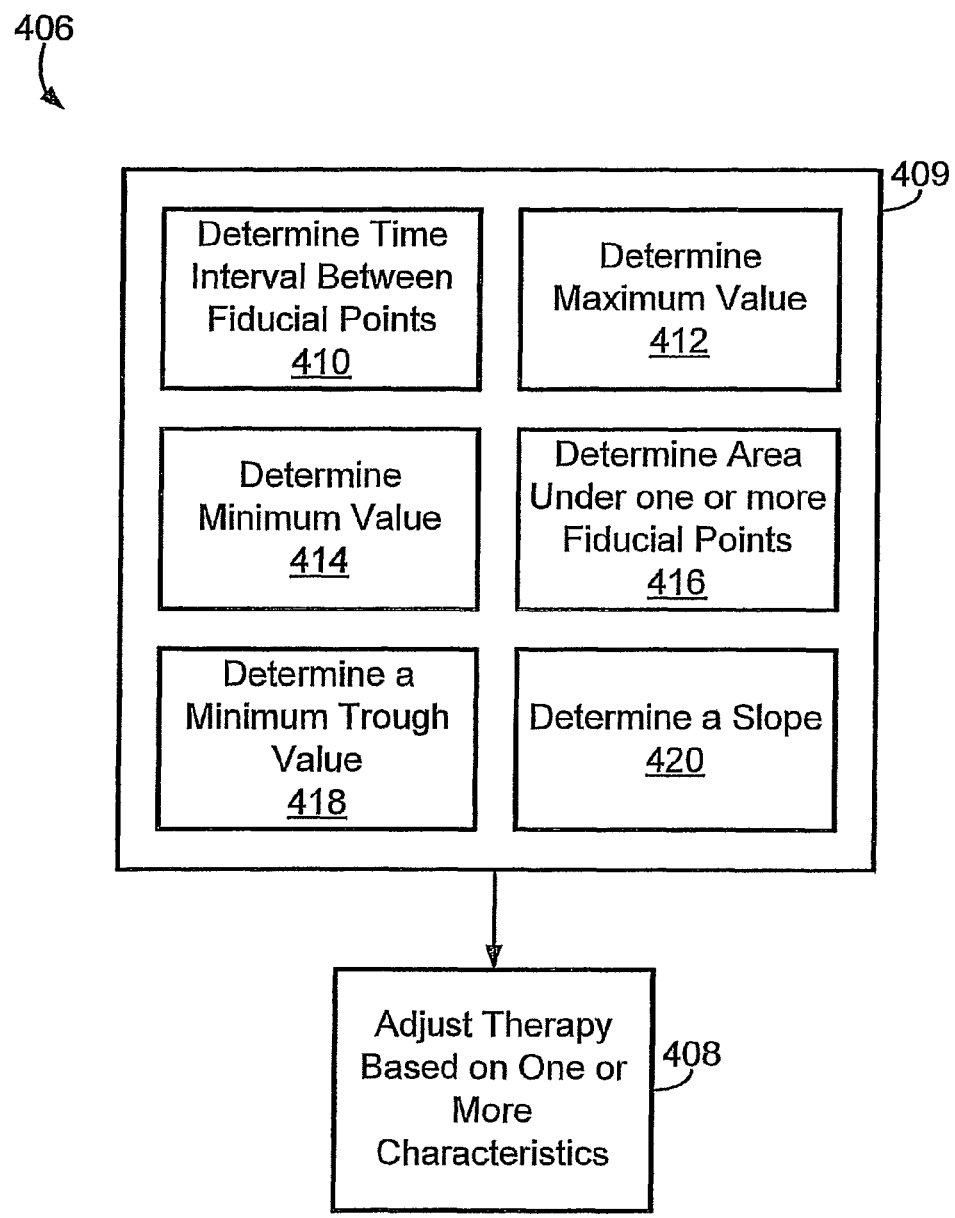
FIG. 11 is a flow diagram of an exemplary method to be used in conjunction with the method of FIG. 10.

Various determinations 409 may be executed as shown in FIG. 11 to monitor a patient and/or deliver cardiac therapy (block 406 of FIG. 10) to the patient based upon the at least one fiducial point. For example, a time interval may be determined between two fiducial points (block 410), a maximum value or local maximum value may be determined (block 412), a minimum value or local minimum value may be determined (block 414), an area under one or more or between two or more fiducial points may be determined (block 416), a minimum trough value may be determined (block 418), a slope may be determined based on two or more fiducial points (block 420) (e.g., the derivative or 2nd derivative of conductance), an integral between two fiducial points, etc.

In at least one embodiment, a myocardial performance index may be calculated using one or more fiducial points determined based on a cardiac impedance signal. The myocardial performance index may be calculated by dividing the sum of the isovolumetric contraction time and isovolumetric relaxation time by the ejection time. As such, in this embodiment, one or more fiducial points (e.g., fiducial points 260, 262, 264, 270 shown in FIG. 6) may be determined and used to estimate the isovolumetric contraction time, isovolumetric relaxation time, and the ejection time, and in turn, the myocardial performance index. Various cardiac therapies may be delivered to the patient based on this myocardial performance index. For example, CRT may be adjusted using the myocardial performance index as known in the art.

In at least another embodiment, pacing mode, pacing rate, pacing location (e.g., using a multipolar LV lead), AV delay, and/or VV delay may be adjusted (block 408) independently or according to a strategic pattern in order to maximize the myocardial performance index or any other heart-related index.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An implantable medical device for use in delivering therapy to a patient's heart comprising:
   at least two electrodes;
   a sensing module configured to monitor an impedance between the at least two electrodes proximate the patient's heart to provide an impedance signal;
   a therapy delivery module configured to deliver cardiac therapy to the patient's heart; and
   a control module coupled to the sensing module and the therapy delivery module and configured to:
      determine one or more fiducial points based on the impedance signal, wherein each of the one or more fiducial points is a fiducial point associated with a mechanical cardiac event during a cardiac cycle, wherein determining one or more fiducial points comprises:

determining a first derivative of the impedance signal to provide a derivative signal;

identifying an E-wave portion of the derivative signal representative of an early diastolic filling phase during a cardiac cycle, identifying an A-wave portion of the derivative signal representative of a late diastolic filling phase during a cardiac cycle, determining at least one A-wave fiducial point of the identified A-wave portion of the derivative signal, determining at least one time interval, wherein the at least one time interval comprises at least one of a duration of the A-wave based on the at least one A-wave fiducial point of the identified A-wave portion of the derivative signal, a time interval between the at least one A-wave fiducial point and at least one E-wave fiducial point of the E-wave portion of the derivative signal, and a time interval between the at least one A-wave fiducial point and at least one other A-wave fiducial point of the A-wave portion of the derivative signal, and deliver cardiac therapy to the patient based upon the at least one time interval.

2. The device of claim 1, wherein the control module is further configured to:
determine at least the time interval between the at least one A-wave fiducial point and the at least one E-wave fiducial point of the E-wave portion of the derivative signal, and
adjust the cardiac therapy delivered to the patient based upon the time interval.

3. The device of claim 2, wherein the control module is further configured to:
determine at least a first maximum value of the derivative of the impedance signal associated with the identified A-wave, and
determine at least a second maximum value of the derivative of the impedance signal associated with the identified E-wave, wherein the time interval between the at least one A-wave fiducial point and the at least one E-wave fiducial point of the E-wave portion of the derivative signal comprises a time interval between the occurrence of the second maximum value and the occurrence of the first maximum value, and
wherein the control module is further configured to adjust the cardiac therapy delivered to the patient based upon the time interval between first and second maximum values.

4. The device of claim 1, wherein the control module is further configured to:
determine a myocardial performance index based on the one or more fiducial points, and
adjust the cardiac therapy delivered to the patient based upon the myocardial performance index.

5. The device of claim 1, wherein the control module is further configured to:
determine at least a first maximum value of the derivative of the impedance signal associated with the identified A-wave,
determine at least a second maximum value of the derivative of the impedance signal associated with the identified E-wave,
determine an E-A minimum trough value between the first maximum value for the E-wave portion and the second maximum value for the A-wave portion, and
adjust the cardiac therapy delivered to the patient based upon the E-A minimum trough value to optimize at least one of AV delay and VV delay.

6. The device of claim 1, wherein the control module is further configured to:
determine an area under at least one of the E-wave portion and the A-wave portion of the derivative signal, and
adjust the cardiac therapy delivered to the patient based upon the area.

7. The device of claim 1, wherein the control module is further configured to:
determine at least one of a first maximum value of the derivative of the impedance signal associated with the identified A-wave and a second maximum value of the derivative of the impedance signal associated with the identified E-wave, and
adjust the cardiac therapy delivered to the patient based upon the at least one time interval and at least one of the first and second maximum values.

8. A method for use in delivering therapy to a patient's heart comprising:
monitoring an impedance between at least two electrodes proximate the patient's heart to provide an impedance signal;
determining one or more fiducial points based on the impedance signal, wherein each of the one or more fiducial points is a fiducial point associated with a mechanical cardiac event during a cardiac cycle, wherein determining one or more fiducial points comprises:
determining a first derivative of the impedance signal to provide a derivative signal;
identifying an E-wave portion of the derivative signal representative of an early diastolic filling phase during a cardiac cycle,
identifying an A-wave portion of the derivative signal representative of a late diastolic filling phase during a cardiac cycle,
determining at least one A-wave fiducial point of the identified A-wave portion of the derivative signal,
determining at least one time interval, wherein the at least one time interval comprises at least one of a duration of the A-wave based on the at least one A-wave fiducial point of the identified A-wave portion of the derivative signal, a time interval between the at least one A-wave fiducial point and at least one E-wave fiducial point of the E-wave portion of the derivative signal, and a time interval between the at least one A-wave fiducial point and at least one other A-wave fiducial point of the A-wave portion of the derivative signal, and
delivering cardiac therapy to the patient based upon the at least one time interval.

9. The method of claim 8, further comprising:
determining at least the time interval between the at least one A-wave fiducial point and the at least one E-wave fiducial point of the E-wave portion of the derivative signal, and
adjusting the cardiac therapy delivered to the patient based upon the time interval.

10. The method of claim 9, wherein determining at least the time interval between the at least one A-wave fiducial point and the at least one E-wave fiducial point of the E-wave portion of the derivative signal comprises:
determining at least a first maximum value of the derivative of the impedance signal associated with the identified A-wave, and determining at least a second maximum value of the derivative of the impedance signal associated with the identified E-wave, wherein the time interval between the at least one A-wave fiducial point and the at least one E-wave fiducial point of the E-wave portion of the derivative signal comprises a time interval between the occurrence of the second maximum value and the occurrence of the first maximum value, and wherein the method further comprises adjusting the cardiac therapy delivered to the patient based upon the time interval between the first and second maximum values.

11. The method of claim 8, further comprising:

determining a myocardial performance index based on the one or more fiducial points, and adjusting the cardiac therapy delivered to the patient based upon the myocardial performance index.

12. The method of claim 8, wherein the method further comprises:

determining at least a first maximum value of the derivative of the impedance signal associated with the identified A-wave, determining at least a second maximum value of the derivative of the impedance signal associated with the identified E-wave, determining an E-A minimum trough value between the first maximum value for the E-wave portion and the second maximum value for the A-wave portion, and adjusting the cardiac therapy delivered to the patient based upon the E-A minimum trough value to optimize at least one of AV delay and VV delay.

13. The method of claim 8, wherein the method further comprises:

determining an area under at least one of the E-wave portion and the A-wave portion of the derivative signal, and adjusting the cardiac therapy delivered to the patient based upon the area.

14. The method of claim 8, wherein the method further comprises:

determining at least one of a first maximum value of the derivative of the impedance signal associated with the identified A-wave and a second maximum value of the derivative of the impedance signal associated with the identified E-wave, and adjusting the cardiac therapy delivered to the patient based upon the at least one time interval and at least one of the first and second maximum values.

\* \* \* \* \*